(12) United States Patent
Odak et al.

(10) Patent No.: US 6,471,855 B1
(45) Date of Patent: Oct. 29, 2002

(54) CASSETTE WITH INTEGRAL SEPARATION DEVICE

(75) Inventors: Sanjay V. Odak, Grayslake; Mark R. Vandlik; Tom Westberg, both of Gurnee, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/718,912

(22) Filed: Nov. 22, 2000

(51) Int. Cl.⁷ .................................................. B01D 17/12
(52) U.S. Cl. .................. 210/143; 210/134; 210/321.68; 210/321.87; 210/416.1; 210/512.1; 694/4.01
(58) Field of Search ..................... 210/97, 134, 321.68, 210/321.87, 512.1, 360.1, 781, 782, 787, 110, 143, 258, 416.1, 646; 604/4.01, 5.01, 6.01, 6.09, 118, 153

(56) References Cited

U.S. PATENT DOCUMENTS

| | | | |
|---|---|---|---|
| 4,083,777 A | * | 4/1978 | Hutchisson ................. 210/646 |
| 4,370,983 A | * | 2/1983 | Lichtenstein ................ 210/929 |
| 4,479,760 A | | 10/1984 | Bilstad et al. |
| 4,479,761 A | | 10/1984 | Bilstad et al. |
| 4,479,762 A | | 10/1984 | Bilstad et al. |
| 5,135,667 A | | 8/1992 | Schoendorfer ............... 210/782 |
| 5,194,145 A | | 3/1993 | Schoendorfer ................ 210/90 |
| 5,462,416 A | | 10/1995 | Dennehey et al. ........... 604/153 |
| 5,634,896 A | | 6/1997 | Bryant et al. .................. 604/29 |
| 5,783,085 A | * | 2/1998 | Fischel ................... 210/321.68 |
| 5,989,423 A | | 11/1999 | Kamen et al. .............. 210/258 |
| 6,270,673 B1 | * | 8/2001 | Belt et al. |

FOREIGN PATENT DOCUMENTS

| | | |
|---|---|---|
| CA | 1210291 | 8/1986 |
| WO | WO01/17584 A1 | 3/2001 |

* cited by examiner

*Primary Examiner*—Joseph W. Drodge
(74) *Attorney, Agent, or Firm*—Gary W. McFarron; Bradford R. L. Price

(57) ABSTRACT

A pneumatic pump manifold disposable system, configured as a cassette, is used for the purpose of red cell and plasma apheresis. The cassette integrates a separation device, manifold system, macro-aggregate filter, and five pumping chambers for the purpose of separating plasma and red cells from the whole blood. The cassette system, with the separation device directly attached without tubing, simplifies the loading of the disposable set into the hardware, and reduces the manufacturing complexity of the set. The system allows for plasma, plasma and red cells, or just red cells to be stored in long term storage containers after a procedure.

41 Claims, 10 Drawing Sheets

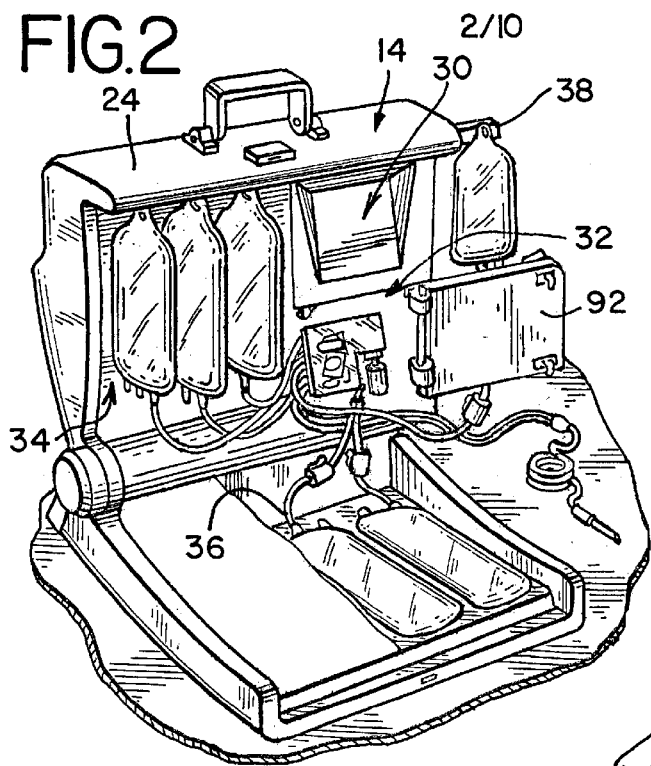
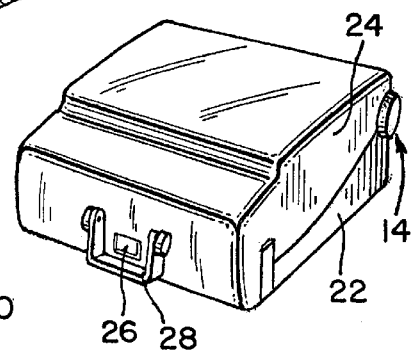
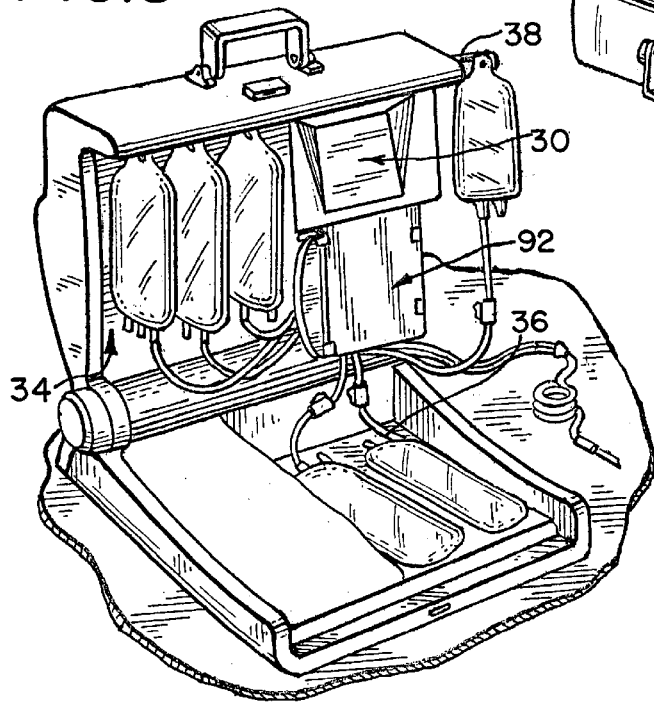

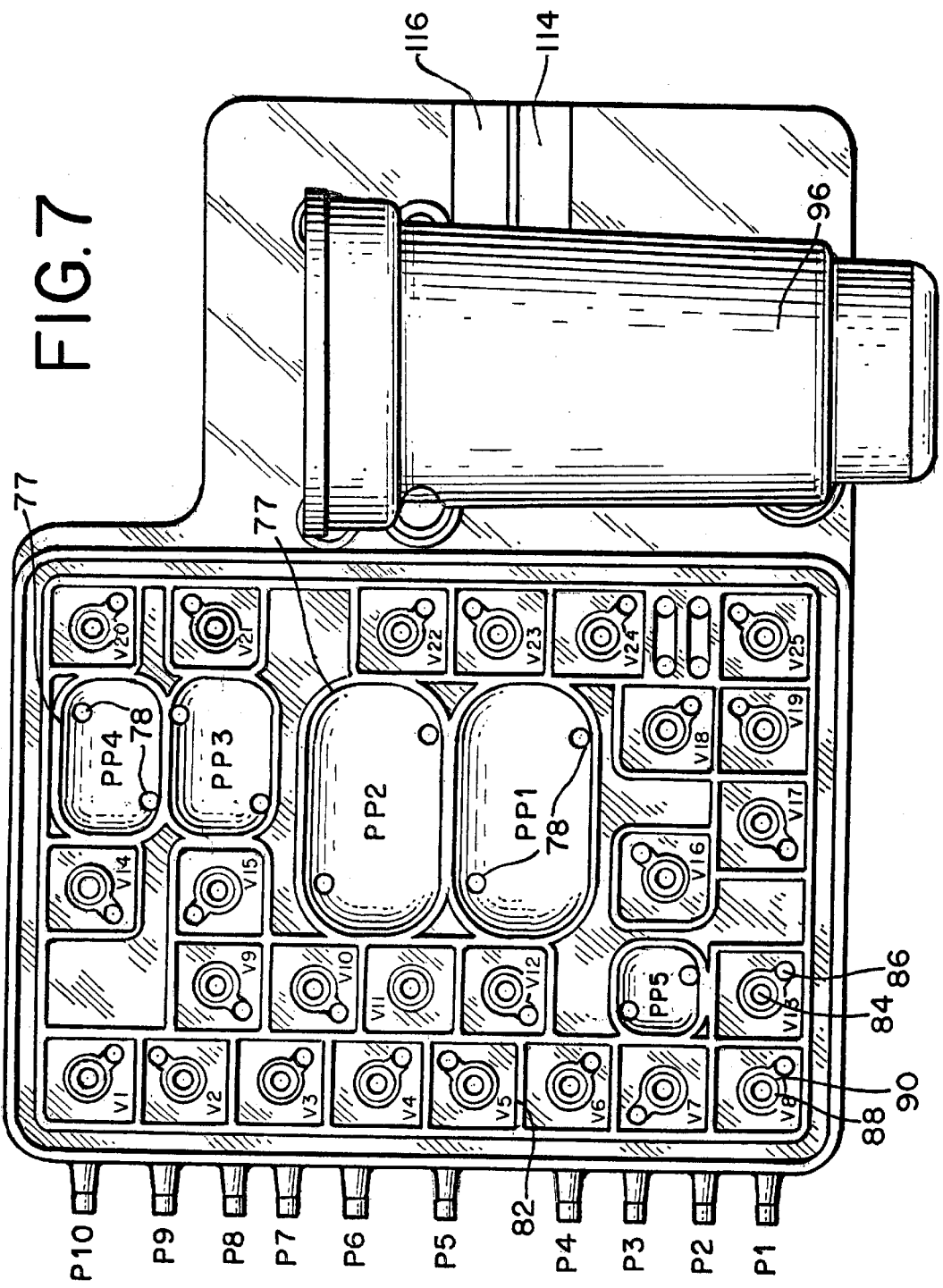

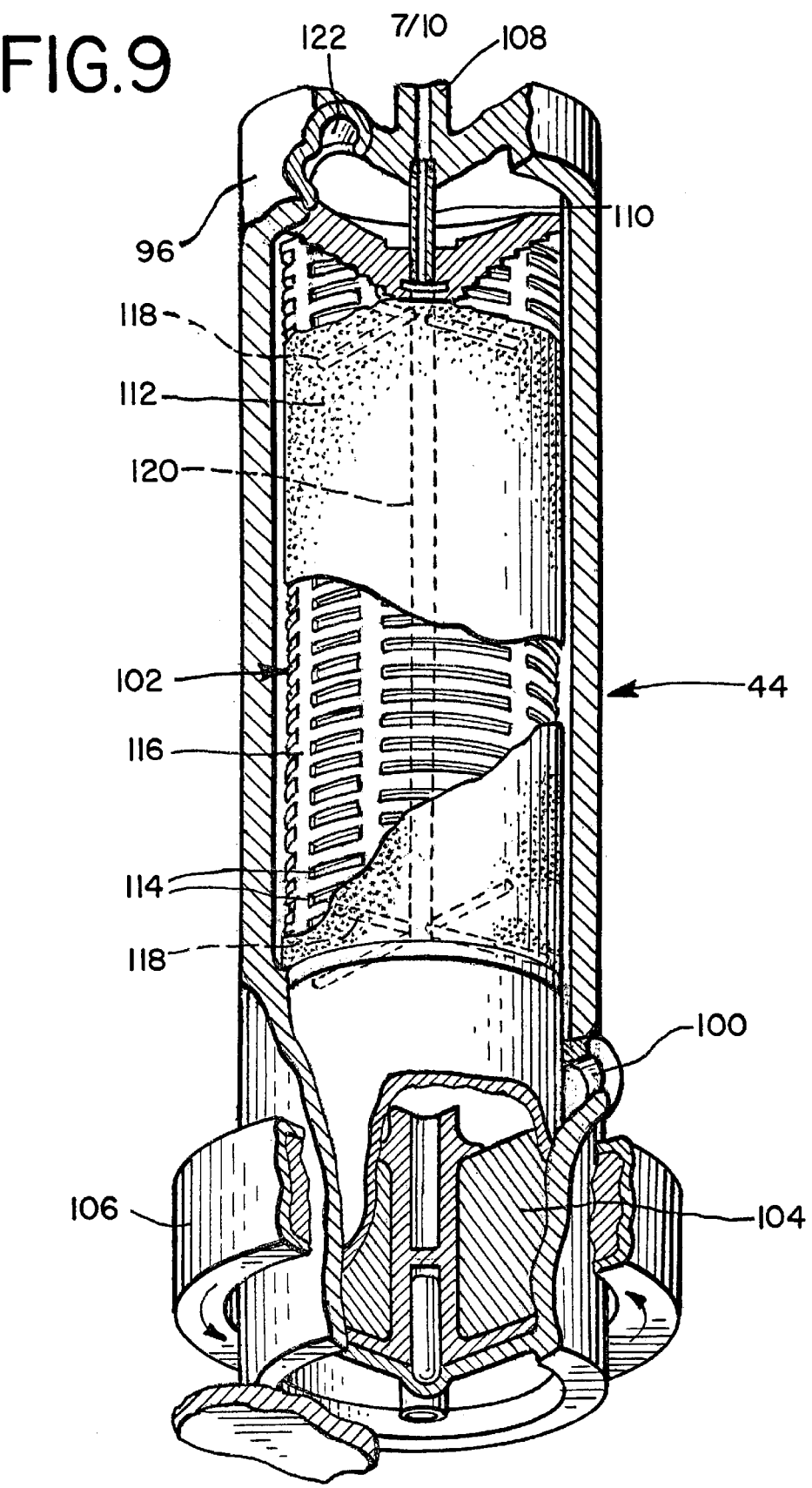

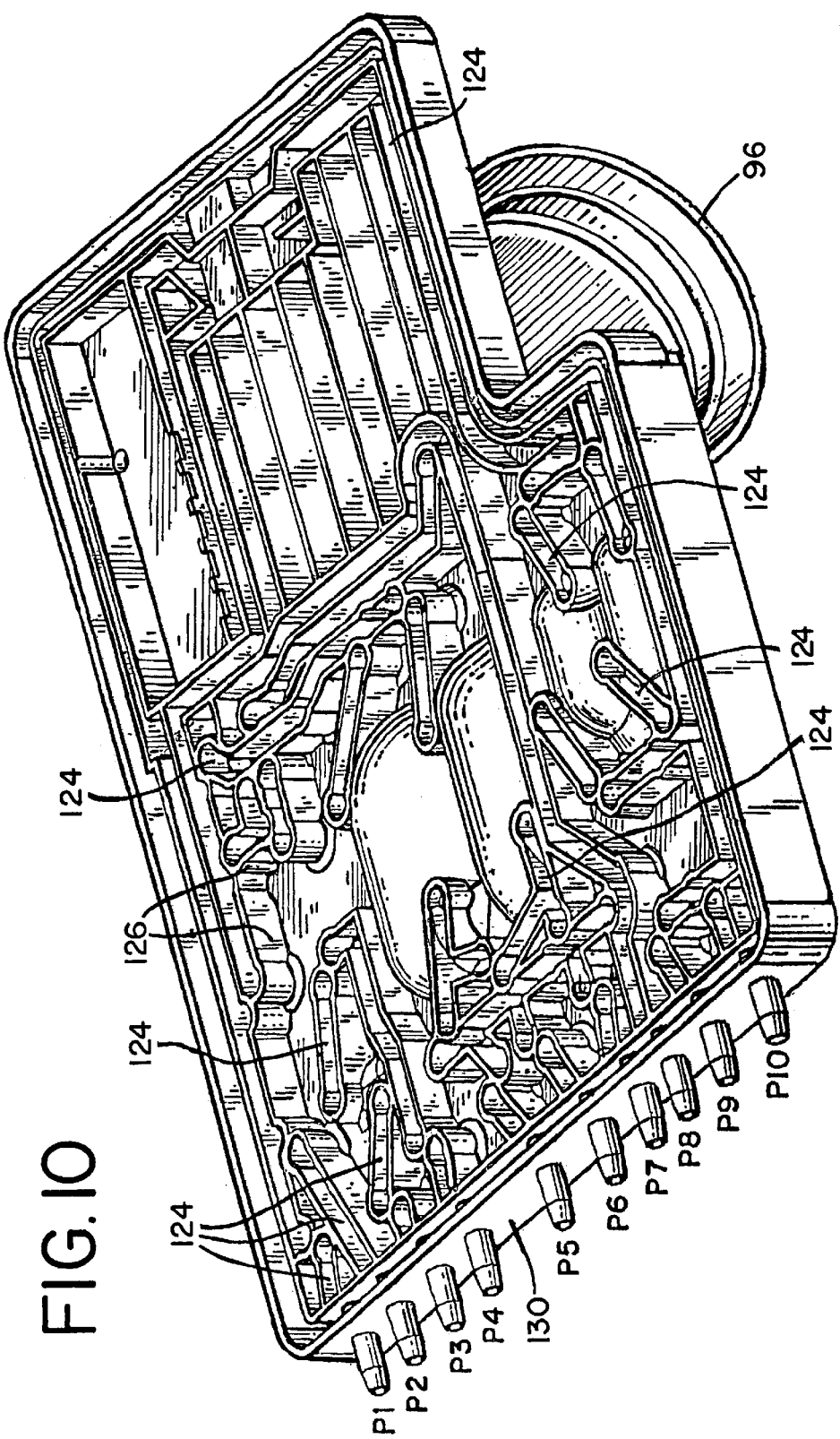

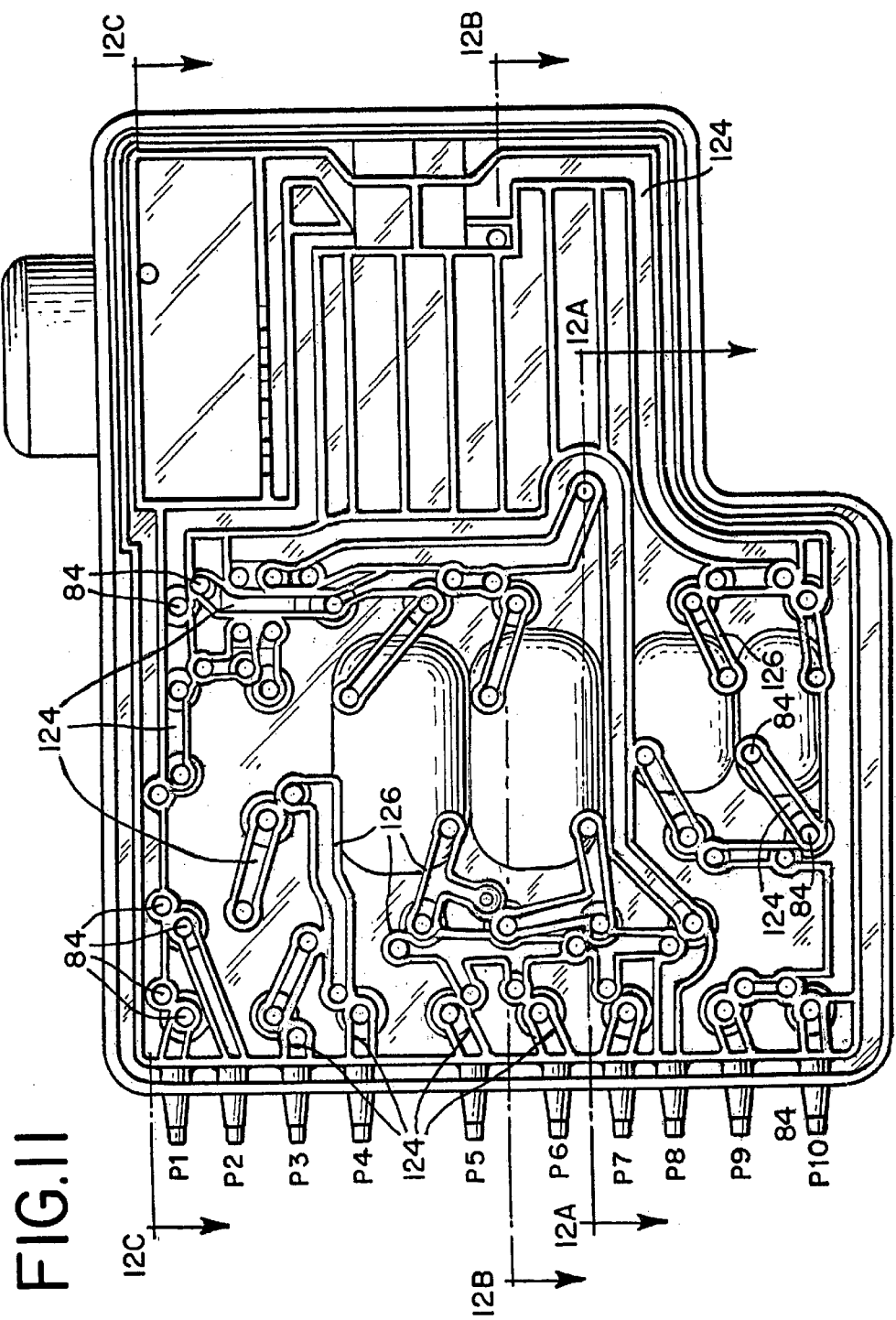

CASSETTE WITH INTEGRAL SEPARATION DEVICE

BACKGROUND OF THE INVENTION

The present invention relates generally to an apparatus for the separation of liquid suspensions, especially suspensions of cellular material such as blood and blood components. More particularly, the invention relates to a novel integral flow control cassette and separation device for the separation or fractionation of one or more constituents of blood.

Broadly speaking, whole blood is a suspension of red blood cells, white blood cells and platelets in liquid plasma. Separation of one or more of the constituents or components of blood from whole blood or from a suspension comprising fewer than all of the usual blood components is referred to as "apheresis." Often, apheresis is carried out at the time of blood collection from a donor—and the collected component is stored for later administration to a patient in need of that blood constituent. Alternatively, apheresis may be used as a therapeutic procedure, wherein the blood component is being withdrawn or depleted as part of the treatment of a patient.

Machines have long been available for automatically processing the blood of donors or patients by withdrawing the desired constituent and returning to the donor or patient the remaining blood components. For example, platelets may be collected from healthy donors and red cells and plasma returned to the donor. Similarly, concentrated red cells may be collected for later transfusion, and platelets and/or plasma returned to the donor. Other procedures may be used for collecting other components, such as plasma or white cells.

Machines for separating blood components, i.e. for performing apheresis, have been based on different operating principles. Centrifugation is one widely-recognized technique, which takes advantage of the slight differences in the density of blood constituents to separate them in a centrifugal field. Commercial apheresis centrifuges include the CS-3000® and Amicus® separators sold by Baxter Healthcare Corporation of Deerfield, Ill., and the Spectra® and Trima® separators by Cobe Laboratories of Golden, Colo. Other manufacturers of commercial blood separators include Fresenius AG, Germany, and Haemonetics Corporation of Braintree, Mass.

Separation of blood components by use of a filter membrane has also been used. One remarkable advance in blood separation technology using membrane filtration has employed a spinning rotor. More particularly, this technique employs the relative rotation between two concentric members and the generation of Taylor vortices in the gap between the relatively rotating members. In a commercial separator employing the principle, marketed as the Autopheresis C® separator by Baxter Healthcare Corporation, the separator includes a membrane-covered spinner, having an interior collection system, disposed within a stationary shell. Anticoagulated blood is fed through a radial gap between the spinner and the shell. Taylor vortices are created in the gap by the spinning roter, and provide an interior sweeping motion which tends to clear the membrane of cellular matter that would otherwise deposit on the membrane and clog the pores. As a result of the membrane cleaning, plasma filtrate can be rapidly extracted through the membrane. U.S. Pat. No. 5,194,145, incorporated by reference herein, more specifically describes the construction and operation of this device.

While both the centrifugation and spinning rotor techniques have worked exceptionally well, the equipment employing the techniques is relatively complicated and operators are required to undergo extensive training. For convenience, health, and safety reasons, blood separation or apheresis machines utilize disposable tubing sets and separation chambers for the separation and collection of the various blood components. The disposable tubing set and separation chamber are mounted on a reusable device which controls flow through the tubing set in accordance with an operator-selected procedure or other operator instruction.

The reusable separation device includes pumps, clamps, sensors and monitors to control flow of blood, blood components and other fluids, such as anticoagulant and saline, through the tubing set and associated separation chamber. Accordingly, it is very important that the tubing set be properly mounted on the hardware to assure proper and safe operation. Due to the large number of guides, pumps, clamps, monitors and sensors onto which the tubing must be carefully mounted, set up of these apheresis devices is often time consuming, tedious, and subject to the possibility of human error. The set-up may be further complicated when the tubing set-up or installation procedure varies with the blood component to be collected. As in any task requiring operator involvement, there is a risk, even if very small, of mis-installation of the tubing set. Although such mis-installation does not typically endanger the donor or patient because of built-in safeguards, it may require time consuming and costly replacement of the tubing set or delay while the operator trouble-shoots and corrects the mis-installation.

Of course, complex tubing sets have the added drawback of being expensive to manufacture because of the intensive amount of labor involved, and the increased vigilance required to assure proper assembly.

Steps have been taken to design apheresis tubing sets that are easier and less time consuming to install, and less subject to error. One example of such a system is the Baxter Amicus® separation system. The Amicus system employs cassettes that are mounted on pump and valving stations on the reusable device, eliminating much of the manual installation of the tubing set. The cassettes have pre-formed passageways that are controlled by the valving stations in accordance with the procedure pre-selected by the operator. An example of this cassette arrangement is disclosed in U.S. Pat. No. 5,462,416, which is incorporated by reference herein.

Although the Amicus system eliminates a significant portion of the tubing set-up steps in the older apheresis devices, it continues to require some mounting steps, as well as assembly of the disposable separation chamber with a reusable centrifuge bowl or chamber in the device. Thus, there continues to be room for more improvement.

In addition to the desire to simplify the tubing set installation procedure, there is a continuing desire to reduce the size and weight of the separation devices. The CS-3000® and Amicus® centrifuges, for example, are relatively large roll-about machines. Although the Amicus® is significantly lighter and easier to move than the CS-3000®, there are many situations where a transportable, such as a small suitcase size, apheresis device would be advantageous. A readily transportable device could have particular application, for example, to blood collection drives which are conducted off-site, at a location away from the main blood bank or hospital laboratory, or to treatment of ill patients who cannot be readily moved and are located where it is not possible to bring a larger apheresis device. Whether the apheresis device is of the conventional size or the transportable type, there remains a need to reduce the possibility for error during the tubing connection process, to reduce or simplify operator training for loading and operation of the equipment, and to reduce manufacturing complexity and cost.

SUMMARY OF THE INVENTION

The present invention is generally embodied in a disposable module adapted for cooperative mounting on a reusable device or module for processing a suspension comprising blood or blood components, and in the system including the disposable module and reusable device. In accordance with the present invention, the disposable module includes an integral flow control cassette and separator. The separator includes a rotor rotatably mounted therewithin, and may be based on a centrifugation, membrane separation or such other rotor-based technique or principle as is desired. The flow control cassette includes an inlet for communicating with a suspension source, and the cassette defines a first flow path communicating between the suspension inlet and an inlet in the separator. A separator outlet is provided for removing a separated portion of the suspension, and the cassette defines a second flow path communicating with the separator outlet.

More specifically, the flow control cassette defines a plurality of flow path segments and a plurality of valve stations interconnecting two or more flow path segments to selectively open or close communication between the segments. The valve stations, which in their broader aspects are operable pneumatically, hydraulically, mechanically or otherwise, are cooperative with the reusable module to control fluid flow through the flow path segments and to define the first and second flow paths. An array of flow path segments and valve stations defined within the cassette may, by operation of the reusable hardware, be selectively connected to provided a variety of different fluid flow configurations, depending on the apheresis process requested.

To move fluid through the disposable flow control cassette may also include pre-formed pump stations, also operable pneumatically, hydraulically, mechanically or otherwise, to pump fluid through the flow path defined by flow path segments and valve stations, as configured by the reusable device in response to a control program for a procedure selected by the user. This arrangement eliminates the routing of tubing through or around pump heads, as required on many prior devices. The integral flow control cassette and separator of the present invention provide a particularly compact arrangement. When the separator is based on the spinning rotor membrane separation principle, the entire disposable module and reusable module can be reduced to the size of a small suitcase, which is readily transportable for off-site collection or depletion procedures.

In a more preferred form, the present invention is embodied in a disposable blood separation set, alone and in combination a reusable actuator device having a plurality of pressure actuators responsive to a control program, in which the separation set includes a cassette including pre-formed pressure actuated pump stations, preformed fluid flow path segments and preformed pressure-actuated valve stations. The cassette also includes an integral fluid separation device communicating with fluid path segments and a plurality of cassette ports communicable with the path segments to convey the flow of fluids to and from the cassette and separation device via flow paths created by the pressure actuators selectively changing pressure to the valve and pump stations in response to a control program. The pressure change to actuate the pump or valve stations may be an increase in pressure such as at or above atmospheric pressure (i.e., a positive pressure), or a decrease in pressure such as to at or below atmospheric pressure (i.e., a negative pressure).

The reusable actuator device or module may be programmable for a plurality of different user-selected separation processes, for example collection of plasma or red cell concentrate or other, and the disposable set can preferably accommodate two or more different blood processing procedures. The cassette in the more preferred form lends itself to different procedures due to the plurality of flow path segments interconnected at valve stations so that selective operation of the valve stations by the actuators establishes the different flow paths needed for different procedures.

More specifically, the cassette may include a rigid plastic base and a flexible membrane covering at least one side of the base. The rigid plastic base includes upstanding walls on one side of the cassette defining valve and pump wells. When the cassette is mounted into the actuator device, the flexible membrane is pressed against the edges of the walls to seal each well to define a closed valve or pump station. Actuators in the reusable device or module control the valving and pumping action by changing the increasing or decreasing pressure applied to the outside surface of the membrane overlying the valves and pump chambers. For example, by increasing pressure against the membrane, it may be pressed against a valve port in the valve well to block flow. Similarly, repeated flexing of the membrane into and out of the pump chamber in response to pressure changes by the actuator may be used to pump fluid through the cassette in sequential draw and pump cycles.

Upstanding walls on the other side of the cassette base define a plurality of flow path segments that extend between valves, pumps and/or separator. These walls may be sealed by a rigid plastic cover or by a flexible membrane as with the one side of the cassette. Thus, fluid flow paths may defined in the cassette for different separation procedures in response to the selected control program in the actuator device by selective pressure changes applied to the flexible membrane at the valve stations, and fluid pumped through the cassette as required for the selected procedure. Accordingly, the same cassette may be used for a variety of different procedures with minimum operator setup required and with greatly reduced opportunity for operator error.

These and other features and aspects of the present invention are set forth below in the detailed description of the attached drawings.

BRIEF DESCRIPTION OF THE DRAWINGS

FIG. 2 is a perspective view of the system shown in FIG. 1, with the door of the reusable module to the pump and valve actuators shown open to accommodate mounting of the disposable module with integral cassette and separator.

FIG. 3 is a perspective view of the system shown in FIG. 1, with the disposable module or processing set fully mounted on the reusable module or processing device and ready for use.

FIG. 4 is a perspective front view of the case that houses the reusable processing device or module shown in FIG. 1, with the lid closed for transporting the device.

FIG. 7 is a plan view of the front side of the integral cassette and separator shown in FIG. 6.

FIG. 9 is a perspective view, partially broken away to show detail, of one type of separator embodiment, but not the only one, that may be employed in accordance with the invention.

FIG. 10 is a perspective view of the back side of the cassette and separator shown in FIG. 6 illustrating preformed fluid flow paths, valve stations and pumping chambers.

FIG. 11 is a plan view of the back side of the cassette and separator shown in FIG. 10.

DETAILED DESCRIPTION OF THE PREFERRED EMBODIMENT

Figure 1:
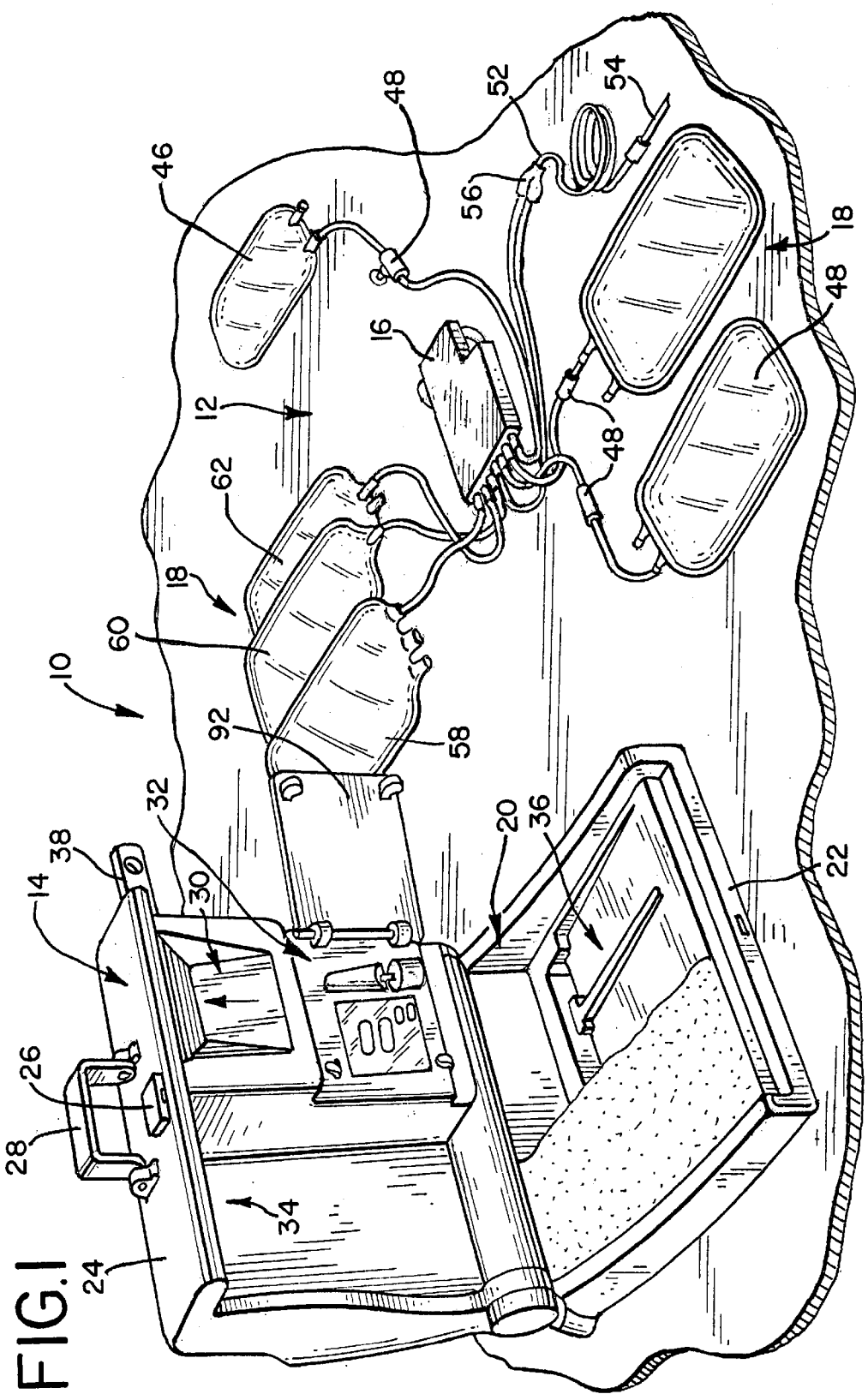
FIG. 1 is a perspective view of a system that embodies features of the present invention, with the disposable module or processing set shown out of association with the reusable module or actuator device (also called a processing device) prior to use.

FIG. 1 illustrates a transportable version of the present invention suitable for carrying to the patient or to an off-site blood collection location. As pointed out earlier, although the present invention is particularly well suited to transportable applications, it is not limited to such applications, and may be employed with significant benefit in larger, less portable systems.

More specifically, FIG. 1 shows an overall blood or blood component processing system 10, which includes a disposable plastic tubing set or fluid circuit module 12 and a reusable controller or device module 14. As will be apparent from the following description, the two modules cooperate to carry out a variety of selected blood processing or collection procedures.

The disposable tubing set or module 12 includes an integral fluid flow cassette and separator, generally at 16, and a plurality of plastic containers, generally at 18, preconnected by flexible plastic tubing to the cassette. As will be described in more detail later, the pre-connected containers may be pre-filled with anticoagulant or saline solutions for use in the collection procedure or may be empty for receiving or storing blood components during or after the separation procedure.

Fluid flow through the tubing set is controlled by the integral cassette and separator in cooperation with the reusable controller or actuator module 14. The controller 14 may be of any desired configuration, and it is shown in a small suitcase style configuration for ease of transporting.

While the fluid circuit module 12 is intended, for safety and convenience, to be disposable after a single use, the controller 14 is intended to be a durable reusable module suitable for long-term use. In the illustrated and preferred embodiment, the controller 14 is mounted inside a portable housing or case 20. The case 20 can be formed into any desired configuration, e.g. by molding, and is preferably made from lightweight, yet durable, plastic material. The case presents a compact footprint, suited for set up and operation upon a table top or other relatively small surface.

The case 20 includes a base 22 and a hinged lid 24, which opens for using (as FIG. 1 shows) and closes for transporting or storing (as FIG. 4 shows). The lid 24 includes a latch 26, for releasably locking the lid 24 closed and a carrying handle 28. In use, the base 22 is intended to rest in a generally horizontal support surface such as a small table or desk.

As noted above, the disposable module 12, including the integral cassette/separator 16, is intended to be sterilized, for one-time use only then discarded. FIG. 1 shows the disposable module 12 prior to installation or assembly onto the reusable module or controller 14. The controller 14 is mounted within the case 20, and may include suspension hooks for liquid filled bags, scales for measuring fluid volumes dispensed or collected, as well as a valve and pump control station to control fluid flow through the cassette and a drive member for the separator device. As shown more specifically in FIG. 2, the case 20 may include a control panel area 30, for operator input and for data display, an actuator area 32 for cooperation with the integral cassette and separator, a recessed bag hanging area 34, an inclined bag rest surface 36, and a scaled hanger 38 for determining volumes dispensed or collected.

The control panel area 30 preferably includes both input and display capabilities. The input capabilities may be in the form of a keypad, touch screen or other suitable input device to allow the operator to input the desired processing information, such as the apheresis procedure to the carried out, patient identification and relevant patient data, desired run time or collection characteristics, or other such information.

The device 14 may be controlled by a programmable microprocessor and include pre-programmed instructions for carrying out several different apheresis procedures, allowing the operator to select from a menu the particular procedure desired or the particular blood component to be collected. The microprocessor may also include data storage capability for storing donor/patient information, processing or collection information and other data for later downloading or compilation.

The control panel area may include an output or display device such as flat screen display, cathode ray tube, light emitting diode, or the like for display of the desired processing information. The output and input capabilities may also be combined in a single feature such as touch panel screen that displays information while simultaneously allowing user input or selection. Data output capability may also include standard parallel or serial ports or other network or ethernet connection capability, as desired, for communication with other computers or networks.

For supporting containers in a hanging position the lid of the case includes the recessed area 34. Hooks (not shown) on the inside of lid 24 provide support for hanging bags of saline, anticoagulant or the like. Similarly, a retractable hanger 38 is provided for supporting a collection bag in which a blood component is at least temporarily stored. Hanger 38 is preferably mounted on a scale located within the lid to allow automated measurement of the amount of blood component collected.

Inclined bag support surface 36 provides additional areas within the case for supporting containers associated with the disposable tubing set or circuit 12. One or more areas of the inclined surface may be heated, if desired, to warm the solution of the bag prior to circulation within the donor or patient.

Taken together, the above features of the controller or reusable module provides a uniquely compact, simple and efficient arrangement for locating and arranging the various components of the disposable module or fluid circuit with reduced opportunity for operator error.

As FIG. 2 shows, before beginning a given blood processing and collection procedure, the operator loads the various components of the tubing set into the case 20. The controller 14 implements the procedure based upon preset software protocols, taking into account other input from the operator. Upon completing the procedure, the operator removes the disposable module. The portion of the module holding the collected blood component or components is removed from the case 20 and retained for storage, transfusion, or further processing. The remainder of the disposable module, after removal from the case 20, is safely discarded.

Figure 5:
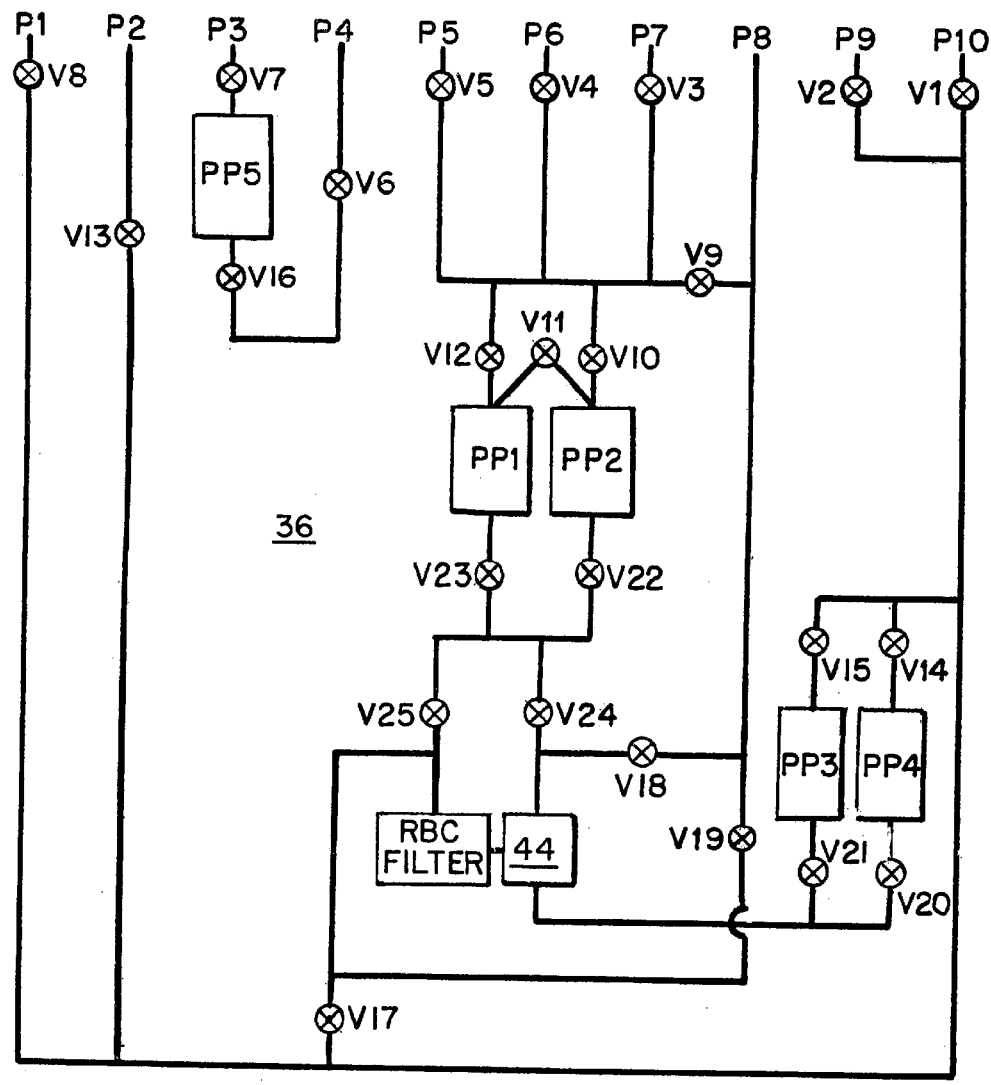
FIG. 5 is a schematic view of a blood processing circuit provided by the disposable module which, in combination with the reusable module of the present invention, can be programmed to perform a variety of different blood processing procedures.

The set 12, in combination with the device 14, defines a programmable blood processing circuit that permits various flow configurations. FIG. 5 schematically shows one representative configuration. Referring to FIG. 5, the system can be programmed to perform a variety of different blood processing procedures, in which, e.g., red blood cells are collected, or plasma is collected, or both plasma and red blood cells are collected, or the buffy coat is collected, or other blood component.

The fluid flow circuit 42 shown in FIG. 5, and defined in the fluid flow cassette, includes several pump stations PP(N), which are interconnected by a pattern of fluid flow path segments through an array of in-line valves V(N). These components provide the capability of pumping at least three fluids simultaneously through the use of three separate pumping systems. The cassette is coupled to the remainder of the disposable tubing set by a plurality of ports P(N).

The circuit 36 defined in the cassette includes a programmable network of flow paths, comprising eight ports P1, P2 and P5 to P10 and four pump stations PP1 to PP4. By selective operation of the line valves V1 to V5, V8 to V15 and V17 to V25, any port can be placed in flow communication with any pump station. By selective operation of the valves, fluid flow can be directed through any pump station in a forward or reverse direction between two valves, or an in-out direction through a single valve.

In the illustrated embodiment, the circuit also includes an isolated flow path comprising two ports P3 and P4 and one pump station PP5. The flow path is termed "isolated," because it cannot be placed (via operation of any valve) into direct flow communication with any other flow path in the fluid flow circuit 42. The pump station PP5 in the isolated flow path is used as a dedicated anticoagulant pump, to draw anticoagulant from a source through port P3 and to meter anticoagulant through P4 into the blood drawn from the patent or donor.

The pneumatic pumping chambers on the cassette are used to move whole blood, blood components, anticoagulant, saline or other solutions, through the fluid circuit and separation device, into storage bags or containers, and possibly back to the donor. The device 14 can be programmed to control flow through circuit 42 by assigning dedicated pumping functions to the various pump stations. For example, in one embodiment, the pump stations PP1 and PP2 may serve as general purpose donor interface pumps, regardless of the particular blood procedure performed, to either draw blood from the donor through port P6, for example, or return blood to the donor through, for example, port P5. Also, these pumps may be actuated exactly out of phase so as to keep the flow of blood smooth. In particular, when one pump draws blood from the donor, the other pump pumps blood to the separator 44 for processing, and then the one pump directs blood to the separator while the other pump withdraws blood from the donor.

Similarly, processed plasma exiting the separator 44 may be acted upon by pump stations PP3 and PP4. Again, these pumps may be actuated exactly out of phase in order to provide a continuous plasma flow. In particular, one pump may draw the plasma from the separator 44 as the other pump pumps plasma to either a sample depository through port P9 or to a plasma collection bag through port P10. For a membrane separation device, these pump stations (PP3 and PP4) may also serve to provide the desired transmembrane pressure (TMP) across the membrane of separator 44 to facilitate processing. For a centrifugal separator, these pumps may assist in maintaining an interface between blood components at a selected position in the centrifuge for the most efficient separation and collection.

In a preferred embodiment, a red blood cell filter (FIG. 5) may include in the cassette to remove the red blood cells after separation of whole blood occurs in the separator 44. The red blood cells can then be either pumped to a temporary or final red cell container through port P8 or port P7. Port P2 provides the necessary means for supplying red cell preservative (such as Baxter Healthcare's Adsol® solution) to any collected red blood cells. Once a predetermined red blood cell count has been reached, as measured, for example by a detector associated with the cassette and controller, the draw process may be stopped and the return to donor process started. During any process, port P1 is available to provide for a means to supply a saline solution through the set and/or as a means to remove waste fluids from the set.

The preferred embodiment includes the ten ports (P1 to P10 of FIG. 5) that connect to flexible tubing of the disposable module 12. As illustrated within FIGS. 1–3, a container 46 holding saline for priming and the like is coupled by plastic tubing to the cassette port P1. A container 48 suitable for holding a red blood cell additive solution is coupled via tubing to the cassette port P2. The tubes connecting these two containers (42,44) may also carry external, manually operated line clamps 48 or internal frangible flow-control connectors, as desired.

A container 50 containing anticoagulant is coupled via tubing to cassette port P3, and also carries a line clamp 48. Port P4 of the anticoagulant circuit is connected to the donor withdrawal and return line 52 which terminates in a needle 54. In the preferred embodiment, the donor tubing line 52 joins, via Y connector 56, with donor return line that communicates with port P5 and the donor draw line that is connected to port P6.

The remaining ports are typically used for the collection of processed fluids. A plasma collection container 58 may be coupled by a tube to the cassette port P10, while the plasma sample port P9 is available for the sampling of processed plasma through a rubber septum (Interlink® connector, or similar) using a syringe, Vacutainer® device or the like. A red blood cell collection container 60 is coupled by a tube to the cassette port P7. A whole blood reservoir 62 may be coupled by a tube to the cassette port P8, to serve as a temporary reservoir for whole blood during processing, but may also serve to receive a second unit of red blood cells for storage.

Thus, the circuit 42 can be programmed, depending upon the objectives of the particular blood processing procedure, to retain all or some of the plasma, the red cells, the buffy coat or the platelets, or to return all or some of those components to the donor.

Figure 6:
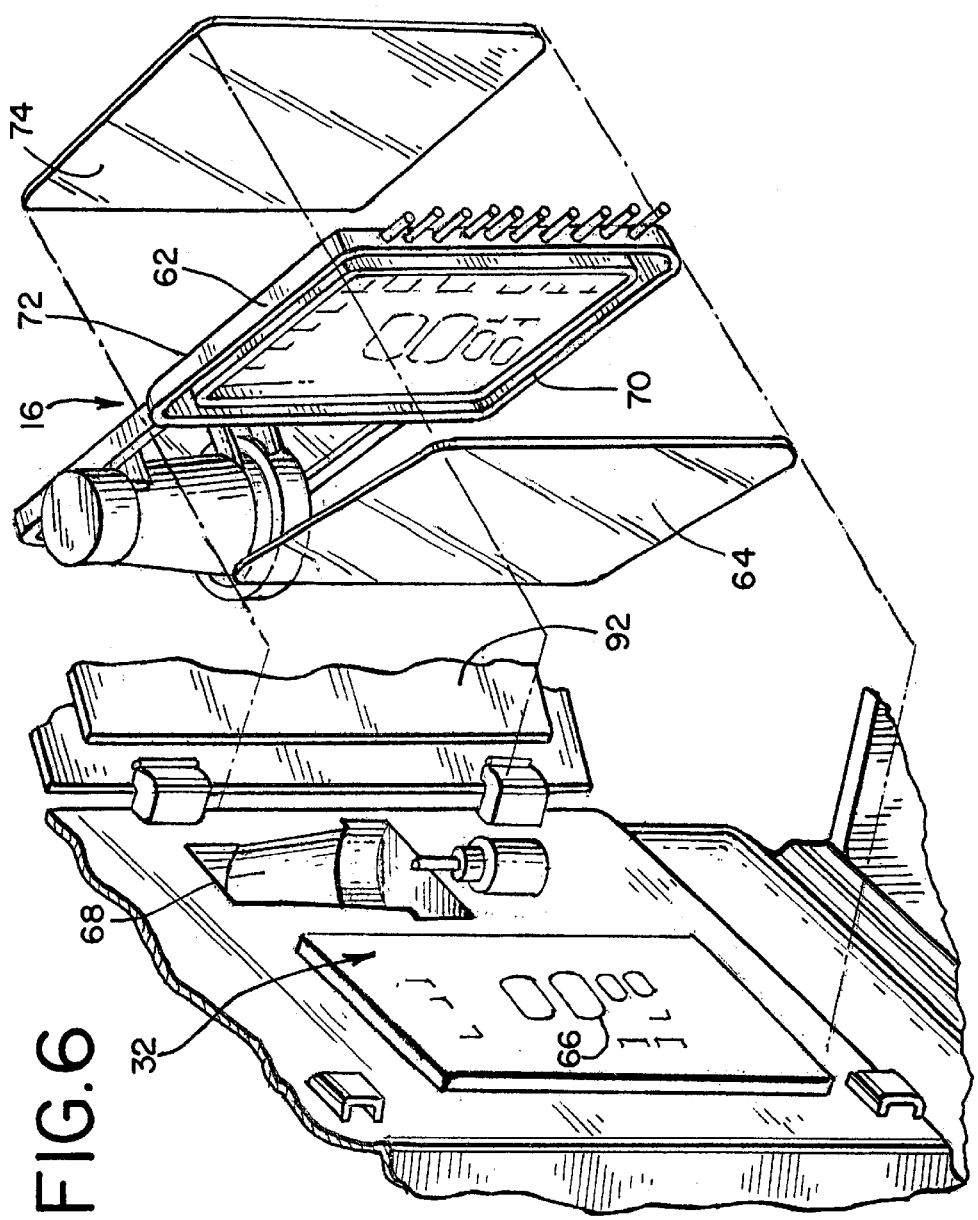
FIG. 6 is an exploded perspective view of an integral cassette (with integral separator) of the present invention, which contains the blood processing circuit shown in FIG. 5, and the pump and valve stations on the reusable processing device shown in FIG. 1.

In a preferred embodiment, the programmable fluid circuit 42 is embodied in the integral cassette and separator 16. FIG. 6 illustrates the mounting of the cassette and separator onto the reusable module or controller 14. The cassette 16 has a base 62 made of a rigid injection molded material (such as acrylic, HD polyethylene, polypropylene, or the like). The cassette is covered on one side by flexible plastic sheeting 64 (such as PVC or the like). The cassette contains preformed flow channel segments, valve and pump stations and porting arrangements to direct the flow of whole blood, saline, anticoagulant, plasma, red cells, and preservative solutions to the correct destinations at the correct time. As a result, the cassette 16 provides a centralized, programmable, integrated platform for all the pumping and valving functions required for a given blood processing procedure. In the illustrated embodiment, the fluid pressure comprises positive and negative pneumatic pressure, although other types of fluid pressure can be used, as well as mechanical actuators if so desired.

As seen in FIG. 6, when loaded, the cassette 16 lies against the actuator area 32 of the reusable module. The actuator area includes an array 66 of valve and pump actuators for controlling the valve and pump stations on the cassette and a separator-receiving area 68 for receiving the separator into operative position on the reusable module. The pump and valve actuators may apply positive or negative pneumatic pressure upon the flexible membrane 64 to control liquid flow through the circuit.

The cassette can take various forms. As illustrated (see FIG. 6) and irrespective of the integral separation device, the cassette 16 comprises the injection molded body or base 62 having a front side 70 and a back side 72. For purposes of the description, the front side 70 is the side of the cassette 16 that, when the cassette is mounted in the reusable module, faces against the actuator area. The flexible diaphragm sheet or membrane 64 overlies the front side 70 while a rigid backing 74 overlies the back side of the cassette in the preferred embodiment.

The cassette body 62 and backing 74 are preferably made of a rigid medical grade plastic material. The diaphragm 64 is preferably made of a flexible sheet of medical grade plastic. The diaphragm 64 is sealed about its periphery to the peripheral edges of the front side of the cassette body 62. Interior regions of the diaphragm 64 can also be permanently or temporarily sealed to the interior regions of the cassette body 62, as described in more detail later.

The cassette body 62 has an array of interior cavities or channels formed on the front and back sides 70 and 72 (see FIGS. 7, 10 and 11). The interior cavities define the valve stations, pump stations and flow paths shown schematically in FIG. 5.

Referring to FIG. 7, the pump stations PP1 to PP5 are formed as large concave wells 76 that are open on the front side 70 of the cassette body 62. Upstanding edges 77 peripherally surround the open wells of the pump stations. The pump wells are closed on the back side 72 of the cassette body 60, except for a spaced pair of through holes 78, which serve as inlet or outlets to each pump chamber for each pump station. The through holes 78 extend through the back side 72 of the cassette body 62. As will become apparent, either through hole can serve its associated pump station as an inlet or an outlet, or both an inlet and outlet.

The in-line valves V1 to V25 are likewise formed in wells that are open on the front side 70 of the cassette base or body.

Each valve well is defined by an upstanding peripheral wall 82 terminates in a raised edge 77 that surrounds the well on the front side of the cassette body. Each valve well also has at least two apertures or through holes 84 and 86 that extend through the cassette body between the front and back sides. The valves are closed on the back side 72 of the cassette body, except for the through holes. As shown in more detail later, one through hole communicates with a selected liquid flow path segment on the back side 72 of the cassette body 62 and the other through hole communicates with another selected liquid flow path segment on the back side of the cassette body.

In each valve, a raised peripheral surface 88 circumscribes one of the through holes to define a valve seat. The peripheral surface is, in turn, bordered by a recessed area 90 that also extends to the other through hole. The flexible diaphragm 64 overlying the front side 70 of the cassette body rests against the edge of the upstanding peripheral walls that surround each of the pump valve stations and valves. With the application of positive force uniformly against this side of the cassette body when it is mounted in the reusable module, the flexible diaphragm 64 seats against the upstanding edges 77, forming a peripheral seal about each of the pump and valve stations. This, in turn, isolates the pumps and valves from each other and the rest of the system.

As pointed out earlier, pressure is applied against the flexible membrane to seal the individual pump and valve stations of the cassette when it is loaded into the reusable module and door 92 of the reusable module is closed. More specifically, the valve and pump actuator area 32 of the reusable module includes surfaces arranged to press against the flexible membrane or diaphragm 64 in the areas of the upstanding peripheral walls 82 that surround each of the valve and pump stations. The door 92 of the reusable module captures the cassette and presses it against the valve and pump actuator area to form the peripheral seals around the pump and valve stations. The control program stored in the reusable module may include a series of pre-run checks to assure that the valve and pump stations are properly sealed by the membrane 64 so there will be no leakage between adjacent valve or pump stations.

With this arrangement, localized application of positive and negative fluid pressures upon the regions of the diaphragm 64 overlying these peripherally sealed valve and pump stations serve to flex the diaphragm in these regions. These localized applications of positive and negative fluid pressures on the diaphragm overlying the pump stations serve to expel liquid out of the pump stations (with application of positive pressure which pushes the membrane into the pump well) and draw liquid into the pump stations (with application of negative pressure which pulls the membrane from the pump well). similarly, localized applications of positive and negative fluid pressure on the diaphragm regions overlying the valves will serve to seat (with application of positive pressure) and unseat (with application of negative pressure) these diaphragm regions against the valve seats, thereby closing and opening the associated valve port. The flexible diaphragm is responsive to an applied negative pressure or even atmospheric pressure for flexure out of the valve seat to open the respective port. The flexible diaphragm is responsive to an applied positive pressure for flexure into the valve seat to close the respective port. Sealing is accomplished by forcing the flexible diaphragm to flex into the recessed valve well to seal against the valve seat that surrounds one of the through holes.

Figure 8A:
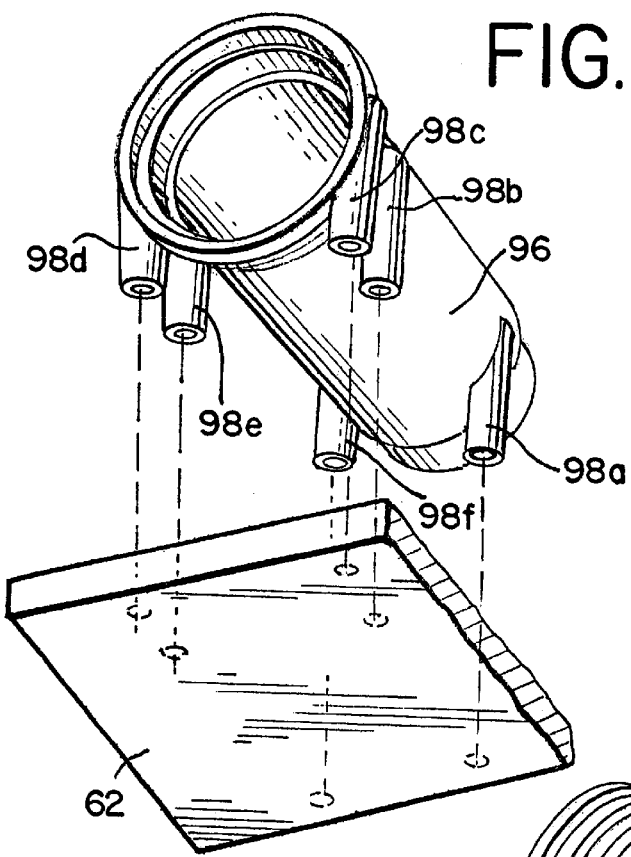
FIGS. 8A–8C are perspective views of the connection of the separator and the cassette.
Figure 8B:
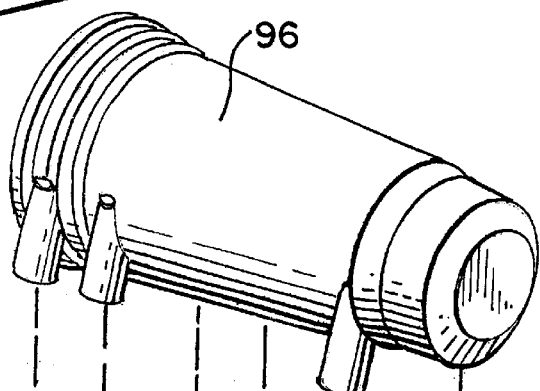
Figure 8C:
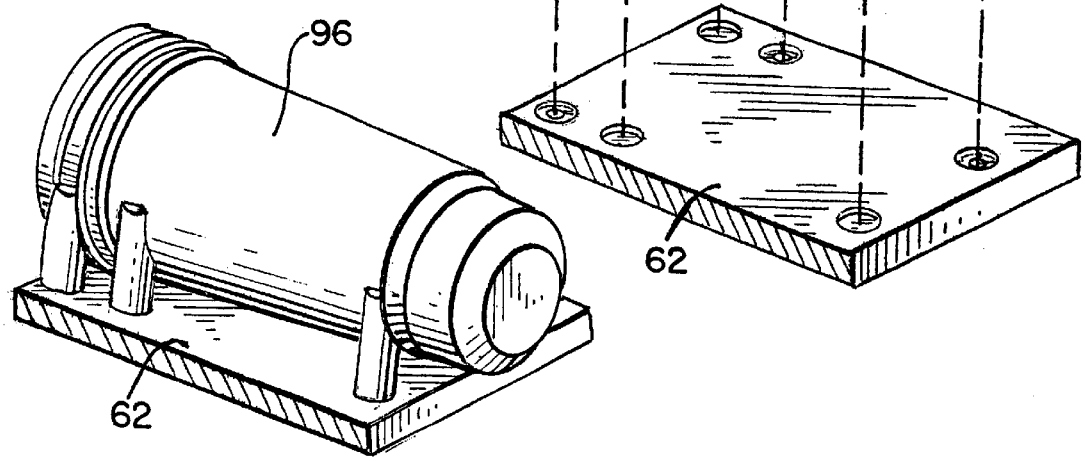
Figure 12A:
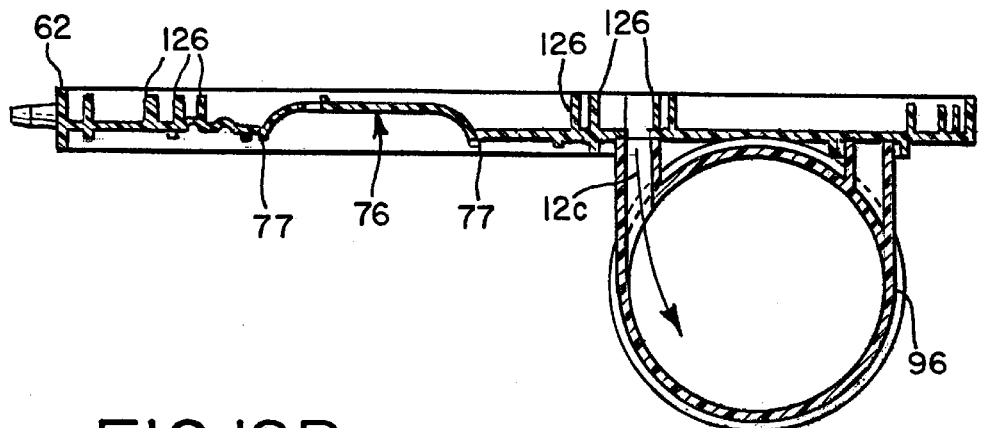
FIGS. 12A–12C are side views, taken along lines 12A–12-A, 12B—12B and 12C—12C respectively of FIG. 11.
Figure 12B:
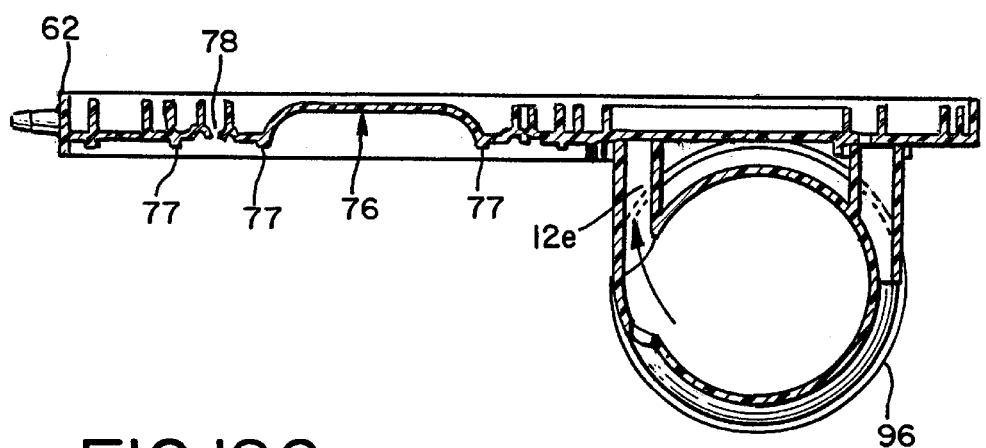
Figure 12C:
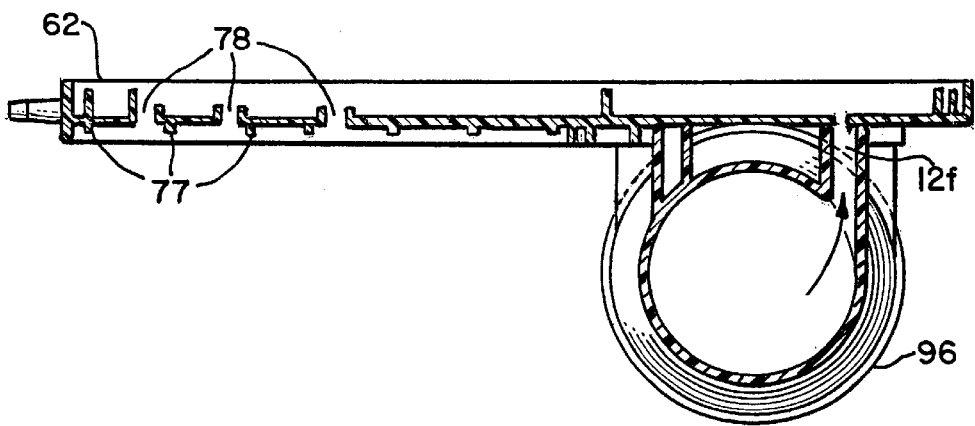

Integral with the cassette body 62 is the separation device or separator 44. The separator 44 in the preferred embodiment, is mounted to the cassette at a separator mounting section 94. Referring to FIGS. 8A–8C, the separation device 44 of the preferred embodiment has an outer generally cylindrical housing 96 with support posts 98 a–f that extend into recesses within the mounting section 94 of the cassette. Posts 98 c, e and f are hollow and provide a fluid flow path between the cassette and separator, as well as support for the separator.

Although the separator 44 may be based on any suitable separation principle, such as centrifugal or membrane separation, the present invention will now be described through the illustration of FIG. 9 with respect to a spinning membrane separator generally comparable in principle to the Autopheresis C® separator sold by Baxter Healthcare Corporation. In particular, the preferred embodiment incorporates a separator much like the one disclosed within U.S. Pat. No. 5,194,145, incorporated herein by reference.

Referring now to FIGS. 9 and 12A–C, whole blood (which may be combined with an anticoagulant) is introduced into the separator 44 at the inlet 100. The separator 44 has a generally cylindrical spinner 102 rotatable about a central longitudinal axis within the stationary housing 96. Magnetic elements 104 attached at one end of the spinner provide for coupling the spinner magnetically to a magnetic driver 106 located within the reusable module. Magnetic drive 106 (not shown in detail) is located at the one end within the reusable module for encompassing and magnetically coupling to the magnetic elements 104 attached to the spinner. The other end of the separator 44 has an port 108 that communicates with the spinner via hollow pivot pin 110.

The surface of the spinner 102 is covered by a filter membrane 112 of a type conventionally used in blood filtration, and having surface apertures in the range of 0.1 to 1.0 microns, preferably in the range of 0.8 to 1.0 microns. Beneath the filter 112, the spinner surface is configured to define a plurality of circumferential grooves 114 interconnected by longitudinal grooves 116, which in turn communicate via radial conduits 118 with a central manifold 120. The manifold 120 is in communication, through an end seal and bearing arrangement (not shown in detail), with the plasma outlet port 108.

As plasma is removed from the blood, the remainder of the blood (high hematocrit blood or red cell concentrate) is removed via a tangential outlet orifice 122 located at the opposite end of the housing from the whole blood inlet 100.

The inlet and outlet ports of the separator communicates via hollow posts 98 c, e and f (best seen in FIGS. 8a–8c) with flow paths or flow path segments 124 formed on the back side 72 of the cassette base or body 62 (best seen in FIG. 10). These flow path segments 124 (see FIGS. 10 and 11) are closed on the front side 70 of the cassette body 62, except where the channel segments intersect the valve stations through holes or apertures 84, or the pump stations through holes or ports 78. The flow path segments 124 are defined by upstanding walls 126 and open outwardly toward the back of the cassette base 62. The open sides of the flow path segments are closed by a rigid plastic cover 128 sealed over the back side of the cassette base 62 and sealed to the edges of the upstanding walls 126 by sonic or adhesive welding or the like. Alternatively, a flexible membrane could be used in place of the rigid cover, with pressure applied against the membrane to seat it against the upstanding walls in a manner similar to membrane sealing used on the front side of the cassette base.

As best seen in FIG. 11, molded ports P1–P10 communicate directly with flow path segments 104 on the back side of the cassette body 62. These flow path segments may be placed in communication with other flow path segments, pump stations or separator by operation of the valve stations to open or block flow between respective segments. The ports P1 to P10 extend out along side edge 130 of the cassette body. As shown in FIGS. 2 and 6, the cassette is vertically mounted in the reusable module and, in this orientation, the ports P1 to P10 are vertically arrayed, one above the other. This ordered orientation of the ports provides a centralized, compact unit aligned with the operative regions of the actuator area.

A selected physical feature or interfering surface on the cassette may allow the hardware to verify, for example by optical detection, that the correct disposable has been loaded for the specific procedure selected, although with the present invention a single disposable set may be used with different procedures.

During operation, measurements of flow rates, collection volumes as well as level monitoring are all accomplished through the hardware and disposable set interface. Flow rates can be measured by at least two means within the system. One simple method is for the control program to count the number of pump strokes, knowing that each stroke pumps a certain volume of fluid. The second means which may be used in combination with the first is based on air flow measurement techniques. The airflow to each pumping chamber can be measured, and hence one can deduce how much fluid is flowing as the fluid flow would be proportional to the volume and pressure of air supplied.

Referring back to FIG. 7, transparent or refractive windows 114 and 116, on the cassette are designed to interface with optical hematocrit and hemolysis detection systems of the hardware, respectively. These windows allow for continuous monitoring of hematocrit and hemolysis levels during any particular procedure, and do not require the operator to input the hematocrit prior to the procedure. Similar windows for monitoring these characteristics such as platelet count or white cell, also could be included in the cassette.

While particular embodiments of the present invention have been shown and described, it will be obvious to those skilled in the art that changes and modifications may be made therein without departing from the invention in its broader aspects.

What is claimed is:

1. A disposable module adapted for cooperative mounting on a reusable module for processing a suspension comprising blood or blood components, said disposable module comprising:

an integral flow control cassette and separator;

said separator comprising a rotor rotatably mounted therein;

said flow control cassette comprising a rigid base and including a suspension inlet for communicating with a suspension source and defining a first closed flow path in said base for direct fluid contact, said first flow path communicating between said suspension inlet and said separator;

said separator and said base being connected to provide a unitary module adapted for mounting onto said reusable module;

said separator including an inlet communicating with said first flow path of said cassette to receive the suspension into said separator;

said separator including an outlet for a separated portion of said suspension; and said cassette defining a second closed flow path in said base for direct fluid contact communicating with said separator outlet.

2. The disposable module of claim 1 in which said flow control cassette defines a plurality of flow path segments and includes a plurality of valve stations interconnecting two or more flow path segments and operable to open or close communication between interconnected flow path segments, said valve stations being cooperative with said reusable module to define said first and second flow paths by selectively opening or closing communication between flow path segments.

3. The module of claim 1 further comprising at least one pump station defined in said cassette base and communicating with at least one of said first and second flow paths, said pump station being cooperative with the reusable module to move fluid through said flow path.

4. The module of claim 3 in which said flow control cassette comprises a flexible film selectively movable by the reusable module into or out of contact with said base to close or open said valve stations and to pump fluid through said pump station.

5. The module of claim 4 in which said rigid base includes a plurality of upstanding walls cooperative with said flexible film to define said flow path segments, valve stations and pump stations.

6. The module of claim 1 in which said separator comprises a housing and a core within said housing, said core and housing being relatively rotatable, said core having an outer surface and said housing having an inner surface spaced from said outer surface to define a circumferential gap therebetween, a microporous membrane mounted on selected of said outer and inner surfaces, said separator outlet communicating with the side of said membrane opposite said gap.

7. The module of claim 6 in which said housing rotates and said core is stationary.

8. The module of claim 6 in which said core rotates and said housing is stationary.

9. The module of claim 1 in which said rotor defines a centrifuge chamber and said separator inlet and outlet communicate with said centrifuge chamber.

10. A suspension processing system, comprising:
   a disposable module having an integral flow control cassette and separator;
   said separator comprising a rotor rotatably mounted therewithin;
   said flow control cassette comprising a rigid base and including a suspension inlet for communicating with a suspension source and defining a first closed flow path in said base for direct fluid contact communicating between said suspension inlet and said separator;
   said separator and said base being connected to provide a unitary module;
   said separator including an inlet communicating with said inlet flow path of said cassette to receive the suspension into said separator;
   said separator including an outlet for a separated portion of said suspension;
   said cassette defining a second closed flow path in said base for direct fluid contact communicating with said separator outlet; and
   a reusable module for receiving said disposable module, said reusable module having a plurality of actuators cooperative with said disposable module for controlling flow through said flow paths for the processing of said suspension.

11. The suspension processing system as defined in claim 10 wherein said reusable module is responsive to a control program.

12. The suspension processing system as defined in claim 10 wherein said reusable module is transportable.

13. The suspension processing system as defined in claim 10 wherein said flow control cassette defines a plurality of flow path segments and includes a plurality of valve stations interconnecting two or more flow path segments and operable to open or close communication between interconnected flow path segments, said valve stations being cooperative with said reusable module to define said first and second flow paths by selectively opening or closing communication between flow path segments.

14. The suspension processing system as defined in claim 13 further comprising at least one pump station defined in said cassette base and communicating with at least one of said first and second flow paths, said pump station being cooperative with the reusable module to move fluid through such flow path.

15. The suspension processing system as defined in claim 14 wherein said flow control cassette comprises a flexible film selectively movable by the reusable module into or out of contact with said base to close or open said valve stations and to pump fluid through said pump station.

16. The suspension processing system of claim 15 in wherein said rigid base includes a plurality of upstanding walls cooperative with said flexible film to define said flow path segments, valve stations and pump stations.

17. The suspension processing system as defined in claim 10 wherein said separator comprises a housing and a core within said housing, said core and housing being relatively rotatable, said core having an outer surface and said housing having an inner surface spaced from said outer surface to define a circumferential gap therebetween, a microporous membrane mounted on selected of said outer and inner surfaces, said separator outlet communicating with the side of said membrane opposite said gap.

18. A suspension processing system as defined in claim 17 wherein said housing rotates and said core is stationary.

19. A suspension processing system as defined in claim 17 wherein said core rotates and said housing is stationary.

20. A disposable blood separation set for installation on an actuator device having a plurality of pressure actuators responsive to a control program, the separation set comprising:
   a cassette including a rigid base and defining in said rigid base pre-formed pressure actuated pump stations, pre-formed closed fluid flow paths for direct fluid contact and pre-formed pressure actuated valve stations interconnecting two or more fluid flow paths;
   a fluid separation device integral with said cassette and in communication with said fluid paths, the separation device and cassette forming a unitary module adapted for installation onto said actuator device; and
   a plurality of cassette ports in direct communication with said flow paths to direct the flow of fluids to and from said cassette and said separation device when the pressure actuators selectively change pressure to said valve and pump stations in response to a control program.

21. A disposable blood separation set as defined in claim 20 wherein said separation device includes a membrane-covered spinner.

22. A disposable blood separation set as defined in claim 20 wherein said separation device includes a centrifuge.

23. A disposable blood separation set as defined in claim 20 wherein said pressure comprises positive and negative pneumatic pressure.

24. A fluid processing system as defined in claim 23 wherein the actuator device is programmable by the control program to place designated fluid flow paths in flow communication with designated pump stations to carry out a selected blood or blood component processing procedure.

25. A fluid processing system as defined in claim 24 wherein the actuator device has a first selectable control program to direct the fluid pressure actuators to apply fluid pressure force to the valve and pump stations to perform a first blood separation procedure, the device further having a second selectable control program to direct the fluid pressure actuators to apply fluid pressure force to the valves and pump stations to perform a second blood separation procedure different than the first blood separation procedure, whereby the same disposable cassette can accommodate the different blood processing procedures.

26. A fluid processing system, comprising:
   a disposable cassette including a rigid base and defining in said rigid base pre-formed pressure actuated pump stations, pre-formed closed fluid flow paths for direct fluid contact and pre-formed pressure actuated valve stations inter-connecting two or more fluid flow paths;
   a fluid separation device integral with said cassette and in communication with said fluid paths, the separation device and cassette forming a unitary module;
   an actuator device for receiving said cassette, said actuator device having a plurality of pressure actuators responsive to a control program; and
   a plurality of cassette ports in communication with said flow paths to direct the flow of fluids to and from said cassette and said separation device when said pressure actuators selectively apply pressure force to said valve and pump stations in response to said control program.

27. A fluid processing system as defined in claim 26 herein said separation device includes a relatively rotatable housing and core with a fluid receiving gap defined between them.

28. A fluid processing system as defined in claim 26 wherein said separation device includes a centrifuge.

29. A fluid processing system as defined in claim 26 wherein said pressure force comprises positive and negative pneumatic pressure.

30. A fluid processing system as defined in claim 26 wherein at least two of said pump stations pump out of phase with respect to each other.

31. A fluid processing system as defined in claim 26 wherein three fluids can be pumped simultaneously.

32. A disposable blood separation set for installation on an actuator device having a plurality of pressure actuators responsive to a control program, the separation set comprising:
   a cassette including a rigid base and defining pre-formed pressure actuated pump stations, pre-formed closed fluid flow paths and pre-formed pressure actuated valve stations;
   a fluid separation device integral with said cassette and in communication with said paths, said separation device having a first generally cylindrical member having a hollow interior and an inner surface, a second generally cylindrical member positioned within said first member, said second member having an outer surface spaced apart from said inner surface of said first member to define a fluid-receiving gap therebetween, one of said paths communicating with said gap, a micro-porous filter membrane disposed on one of said surfaces for passing a filtrate therethrough, one of said paths communicating with said filtrate passing through said membrane, rotating means coupled to one of said members for driving the rotating member at a rate selected to establish annular vortices within said gap, the separation device and cassette forming a unitary module adapted for installation onto said actuator device; and
   a plurality of cassette ports in communicable with said flow paths to convey the flow of fluids to and from said cassette and said separation device when said pressure actuators selectively apply pressure force to said valve and pump stations in response to the control program.

33. A disposable blood separation set as defined in claim 32 wherein said pressure force comprises positive and negative pneumatic pressure.

34. A disposable blood separation set as defined in claim 32 wherein three fluids can be pumped simultaneously.

35. A disposable blood separation set as defined in claim 32 wherein said rotating means comprises a drive member adapted to be magnetically coupled to actuator device.

36. A fluid processing system, comprising:
   a disposable cassette including a rigid base and defining pre-formed pressure actuated pump stations, pre-formed fluid flow paths and pre-formed pressure actuated valve stations;
   a fluid separation device integral with said cassette and in communication with said paths, said separation device having a first generally cylindrical member having a hollow interior and an inner surface, a second generally cylindrical member positioned within said first member, said second member having an outer surface spaced apart from said inner surface of said first member to define a fluid-receiving gap therebetween, one of said paths communicating with said gap, a micro porous filter membrane disposed on one of said surfaces for passing a filtrate therethrough, one of said paths communicating with said filtrate passing through said membrane, rotating means coupled to one of said members for driving the rotating member at a rate selected to establish annular vortices within said gap, the separation device and cassette forming a rigid unitary structure;
   an actuator device for receiving said cassette, said actuator device having a plurality of pressure actuators responsive to a control program; and
   a plurality of cassette ports in communicable with said flow paths to convey the flow of fluids to and from said cassette and said separation device when said pressure actuators selectively apply pressure force to said valve and pump stations in response to said control program.

37. A fluid processing system as defined in claim 36 wherein the actuator device is programmable by the control program to place selected fluid flow paths in flow communication with selected pump stations to carry out a blood processing procedure.

38. A fluid processing system as defined in claim 37 wherein the actuator device has a first selectable control program to direct the fluid pressure actuator to apply fluid pressure force to the valve and pump stations to perform a first blood separation procedure, the device further having a second selectable control program to direct the fluid pressure actuator to apply fluid pressure force to the valves and pump stations to perform a second blood separation procedure different than the first blood separation procedure, whereby the same disposable set can accommodate different blood processing procedures.

39. A fluid processing system as defined in claim 37 wherein three fluids can be pumped simultaneously.

40. A fluid processing system as defined in claim 36 wherein said pressure force comprises positive and negative pneumatic pressure.

41. A fluid processing system as defined in claim 36 wherein at least two of said pump stations pump out of phase with respect to each other.

* * * * *